(12) United States Patent
Stark et al.

(10) Patent No.: US 8,282,911 B2
(45) Date of Patent: Oct. 9, 2012

(54) IMPLANT MATERIAL

(75) Inventors: Jan W. Stark, Zurich (CH); Oliver Schneider, Untersiggenthal (CH); Stefan Loher, Montlingen (CH); Tobias Brunner, Zurich (CH); Marc Simonet, Lenzerheide (CH); Patrick Schmidlin, Oberdürnten (CH); Robert N. Grass, Zurich (CH)

(73) Assignees: ETH Zürich, Zürich (CH); Universitat Zürich, Zürich (CH)

( * ) Notice: Subject to any disclaimer, the term of this patent is extended or adjusted under 35 U.S.C. 154(b) by 549 days.

(21) Appl. No.: 12/446,558

(22) PCT Filed: Oct. 23, 2006

(86) PCT No.: PCT/CH2006/000589
§ 371 (c)(1),
(2), (4) Date: Jun. 1, 2009

(87) PCT Pub. No.: WO2008/049242
PCT Pub. Date: May 2, 2008

(65) Prior Publication Data
US 2010/0196440 A1    Aug. 5, 2010

(51) Int. Cl.
*A61K 8/00* (2006.01)
(52) U.S. Cl. .................. 424/70.1; 424/78.08; 424/78.17
(58) Field of Classification Search .................. None
See application file for complete search history.

(56) References Cited

U.S. PATENT DOCUMENTS

| | | | |
|---|---|---|---|
| 4,595,713 A | 6/1986 | St. John | |
| 4,859,383 A | 8/1989 | Dillon | |
| 5,007,930 A | 4/1991 | Dorman et al. | |
| 5,508,342 A | 4/1996 | Antonucci et al. | |
| 5,955,529 A | 9/1999 | Imai et al. | |
| 6,302,913 B1 * | 10/2001 | Ripamonti et al. | 623/16.11 |
| 6,384,197 B1 | 5/2002 | Weis et al. | |
| 2001/0016772 A1 | 8/2001 | Lee et al. | |
| 2003/0082808 A1 | 5/2003 | Guan et al. | |
| 2003/0232071 A1 | 12/2003 | Gower et al. | |
| 2004/0249015 A1 | 12/2004 | Jia et al. | |
| 2004/0258732 A1 | 12/2004 | Shikinami | |
| 2005/0053638 A1 | 3/2005 | Tanaka et al. | |
| 2005/0100581 A1 | 5/2005 | Laurencin et al. | |
| 2005/0112349 A1 | 5/2005 | Laurencin et al. | |
| 2005/0226904 A1 | 10/2005 | Choi et al. | |
| 2005/0240281 A1 | 10/2005 | Slivka et al. | |
| 2006/0008504 A1 | 1/2006 | Kerr et al. | |
| 2006/0172918 A1 | 8/2006 | Sotome et al. | |
| 2006/0204738 A1 * | 9/2006 | Dubrow et al. | 428/292.1 |

FOREIGN PATENT DOCUMENTS

| | | |
|---|---|---|
| EP | 1 437 148 | 7/2004 |
| WO | WO2005073289 | 8/2005 |
| WO | WO2005087660 | 9/2005 |

OTHER PUBLICATIONS

Katakam et al. "Processing of calcium phosphate based functionally graded bioceramics using microwaves", 2003, Trends Biomaterial Artificial Organs, vol. 17 issue 1, pp. 24-27.*
Loher et al., "Improved degradation and bioactivity of amorphous aerosol derived tricalcium phosphate nanoparticles in poly(lactide-co-glucolide)," *Nanotechnology*, 17(8) 2054-2061, Apr. 2006.
Nair et al., "Development of Novel Tissue Engineering Scaffolds via Electrospinning," *Expert Opinion on Biological Therapy*, 4(5):659-668, May 2004.
Huinan et al., "Increased osteoblast functions on nanophase titania dispersed in poly-lactic-co-glycolic acid composites," *Nanotechnology*, 16(7):S601-S608. Jul. 2005.
International Search Report in corresponding PCT/CH2006/000589, Jun. 28, 2007.

* cited by examiner

*Primary Examiner* — James Rogers
(74) *Attorney, Agent, or Firm* — Marshall, Gerstein & Borun LLP

(57) ABSTRACT

The present relates to the field of dental and bone surgery. In particular, the invention relates to fibrous pharmaceutical compositions; fibrous webs, yarns and woven fabrics of such pharmaceutical compositions; to implant material essentially consisting of fibrous pharmaceutical compositions; to the manufacturing and use of such fibers/webs/implant materials.

10 Claims, 5 Drawing Sheets

IMPLANT MATERIAL

This application is the U.S. National Stage of International Application No. PCT/CH2006/000589, filed Oct. 23, 2006.

The present relates to the field of dental and bone surgery. In particular, the invention relates to fibrous pharmaceutical compositions; fibrous webs of such pharmaceutical compositions; to implant material essentially consisting of fibrous pharmaceutical compositions; to the manufacturing and use of such fibers/webs/implant materials.

Materials for dental and bone surgery. Next to numerous permanently implanted materials both consisting of ceramic, metals, polymers or combinations of two or all three, more recent development has started to provide biodegradable materials that remain only temporarily in the human body. Many of the investigated materials are partly or fully composed of calcium phosphates, such as hydroxyapatite or tricalcium phosphate (TCP) tracing back to the fact that bone mineral mainly consists of a complex form of carbonated hydroxyapatite. Moreover, such materials are considered osteoconductive and allow for direct bonding to bone while in some cases they were even assumed to be precursors to bone apatite formation. These materials are slowly dissolved and can successively be re-sorbed, degraded and replaced by own tissue from the patient. More specifically, dental and bone surgery has strongly profited from the development of degradable implants, especially for the treatment of younger patients (0-60 years). Within most application, a bone implant material is used to fill a defect (loss of natural bone at a given site in the skeleton or dental parts) or sustain a specific function (e.g. keep an artificial hip implant in place and transfer the forces from the leg onto the implanted shaft). More specifically, the area of degradable materials can be divided from a materials point of view into the following major material groups Degradable Metal implants (which are not relevant in the context of the present invention); Degradable Polymer implants and Degradable. Ceramic implants and Degradable Composites.

Degradable Polymer implants: Unfortunately the clinical applications of many prefabricated hard bioactive calcium phosphate ceramics are limited because of their brittleness, incompressibility and difficulty in shaping. Bone cements are often used for the repair of bony defects because of their easy application by injection. However, such systems normally entail setting times of approximately 15 minutes and often lack reasonable resorption capacity due to hindered accessibility of the dense, hardened cement. A solution to overcome the brittleness of pure ceramic biomaterials is the use of polymers as a base material for composites or in pure form. Preferably, biodegradable polymers are chosen since the trend of today's reconstructive surgery clearly tends towards the use of bioresorbable implant materials which fulfill their task for a given time period and are continuously replaced by regenerating tissue. This prevents the patient from secondary surgical interventions, minimizing postoperative stress as well as treatment expenses. Among biocompatible and bioresorbable polymers, poly(lactide-co-glycolide) (PLGA) has attracted attention due to its potential applications in drug delivery, soft tissue engineering, nerve regeneration and orthopedics. Pure polymer implants are based on hydrolysable polymers, proteins, combinations thereof and can be made from artificial or natural sources. These materials are often flexible, optionally soft and are manufactured in numerous shapes, e.g. fibers, blocks, as pastes, curable pastes, membranes and others. Their flexibility offers a huge advantage since during surgery, the material is easily adapted to the geometry of a bone defect or the space between an implant and remaining bone.

Degradable Ceramic implants: Most of the ceramic implants are based on partially soluble or instable calcium based salts. By far the most important materials are calcium phosphates, sulfates or carbonates. Amongst the calcium phosphate, mainly tricalcium phosphate has attracted tremendous interest since it degrades rapidly within the human bone, preferable if the so called beta phase is applied. Numerous patent applications and a large body of scientific literature have arisen from these developments. Due to, their mechanical characteristics, ceramics are generally hard, often brittle and can not be readily adapted to a geometry as they are not soft or flexible. This limits their applicability and most materials are either supplied as cements (soft, but chemical reaction within body required to finish the formation process), blocks (require shape giving e.g. by sawing), granules or powders (can fill a defect, but stay loose within the bone defect).

Degradable Composites: The currently known composites are either rigid or have to be applied in a granulate form. Presently, there exist numerous ways to prepare composite materials consisting of at least one ceramic constituent and at least one polymer matrix. The most important group of materials consists of a continuous polymer matrix with inter-dispersed ceramic material. Materials where the ceramic is the continuous phase should more adequately be described as coated ceramics and compose a different set of materials with other useful properties. Ambrosio et al. [1] and Khan et al. [2] disclose a method to in-situ form amorphous calcium phosphate in PLGA microspheres by a modified emulsion/solvent evaporation technique. The composite microspheres can be subsequently sintered to a porous 3D-scaffold. Loher et al [3] disclose dense (non-porous) PLGA films doped with amorphous tricalcium phosphate nanoparticles and investigated the in vitro biodegradation of such materials. U.S. Pat. No. 7,022,522 describes a polymer scaffolds comprising an extensively interconnected macroporous network with macropores of 0.5 to 3.5 mm, preferably 1.0 to 2.0 mm. Optionally, the polymer can contain calcium phosphate particles. US 2005053638 describes fibrous composites of calcium phosphate in a collagen matrix. US 2004258732 describes a uniformly dispersed composite consisting of a nonwoven fabric-like aggregate that is formed from a mixed solution prepared by dissolving a biodegradable and bioresorbable polymer in a volatile solvent and dispersing a bioactive bioceramic powder therein, this is formed into a porous fiber aggregate molding by compression-molding it under heating, the fiber aggregate molding is soaked in the volatile solvent and then said solvent is removed.

In most cases the surgeon does not exactly know prior to operation, what kind/type/size of implant will be required. Hard, ceramic implants are currently shaped by sawing/drilling/chipping and other mechanical methods during the operation. This results in prolonged duration of the operation, higher secondary risks for the patient, risks to entrain impurities, risk of infections and higher costs per surgical correction. Thus, there is a need for implants that reduce the duration of an operation and/or reduce secondary risks.

Further, most load-bearing implants are introduced into the body in a bone or joint and need to be connected to the remaining or existing tissue of the patient. In the case of most bone implants, a most intimate contact between the implant and the remaining bone is most important for successful and fast healing. Moreover, holes between the implant and the remaining bone may give rise to inflammation, tissue necrosis and often result in most painful effects for the patient. Similarly, in dental surgery where most corrections are much smaller than e.g. in hip or knee implants, the surgeon ideally avoids destruction or loss of bone tissue as far as possible. Fine corrections are crucial to regain or maintain correct bite geometry in a dental correction. More specifically, many corrections require a change in bone geometry, more bone, less bone or the incorporation of a screw/root replacement etc into existing bone tissue. Unfortunately, the presently used hard, non-flexible implants are not well suited for this type of corrections. Similarly, hard implants are difficult to intimately match to existing bone geometry. Alternatively, today mainly polymerizable cements are used to fill this gap between implant and existing bone. Latter cements are either mechanically stable but not degradable and result in inflammation, limited lifetime and/or do not promote active in-growth of patient bone. Or, alternative cements are mainly inorganic or composite but mechanically not stable enough for load bearing. All existing materials are rather dense and introduce large amounts of alien substances per volume (typically over 1 g per cm$^3$).

Cements that fulfill one or more of these requirements are known. Such cements are generally made from a soft, pasty or liquid raw formulation that can either be initiated by addition of an initiator, mixing with other components, heating or other means and then harden at the site of application. These properties are quite ideal for many applications as small and difficult-to-access sections within a site of operation can be reached easily. Cements exist as mainly organic, both degradable or permanent, inorganic formulations (one or multiple components) or composites. Surgical experience, however, has shown that next to some of their most advantageous properties, cements also have limitations. Depending on the application, the skillful surgeon recognizes the need for other flexible implants and may decide against using a cement. More specifically, cements can be a problem in the following situations:

i) filling of a defect with connection to an open (air or liquid filled) cavity (e.g. sinus cavity) where the injection must be confined within a specific area (spilled cement would cause unfavorable side-effects);

ii) filling of a defect or gap between an implant and neighboring tissue where some mechanical flexibility is preferred throughout the healing process. Here, a cement would result in a hard bond. Such partially flexible connections are mainly avoiding in-growth of scar- and inflammatory tissues. The minor movement of the filler with the adjacent bone can be supportive on the auto-regeneration of the tissue.

iii) filling of a defect, gap or hole where only a minimal amount (mass) of alien substance shall be incorporated. This requires a bulk density as low as possible.

iv) filling of a defect, gap or hole where the cavity shall additionally be enriched with patient-own stem cells as to trigger auto-regeneration of this tissue. Here, the flexibility and low density are key as they allow the mechanical stimulation of the bone marrow stem cells and supply the required ions (e.g. calcium and phosphate). Most cements are at least in parts cytotoxic, or they release heat during hardening which can kill cells.

Thus, it is an aim of the present invention to provide materials that overcome the limitations and disadvantages of the currently known materials. Further, it is an aim of the present invention, to provide processes for obtaining such materials and uses for the materials provided.

While there are shown and described presently preferred embodiments of the invention, it is to be distinctly understood that the invention is not limited thereto but may be otherwise variously embodied and practiced within the scope of the following claims. Further, it is understood that the various ranges, embodiments, and preferences provided in this specification may be combined at will. Also, specific embodiments or preferences may not apply.

Unless otherwise stated, the following definitions shall apply in this specification:

The term "fibers" is generally known. It denotes the primary shape of the material obtained by a process according to the invention. Typically the fibers obtained have a circular profile; diameter may vary but are usually between 1 and 50 um; preferably between 2 and 20 um. Typically, the ratio of length:diameter is above 100:1. Typically, fibers are flexible. FIGS. 2 and 3 show such fibers.

The expression "fibrous web" denotes a non-woven material essentially consisting of fibers. Typically, such fibrous webs have an open structured, highly accessible network of fibers. Examples are also shown in FIGS. 1c, 2 and 3. Typically, such fibrous webs are compressible.

The term "biodegradable" is known in the field. In general it refers to material that can be degraded by a living organism; in the context of this invention in particular by the human/animal body. One has to distinguish between biodegradation of organic matter (e.g. polymers) and inorganic matter (e.g. ceramics). Biodegradation of organic matter proceeds first via a decomposition process (hydrolysis) either enzymatically or nonenzymatically into nontoxic products (i.e. monomers or oligomers) and further is eliminated from the body or metabolized therein [Hayashi, T., "Biodegradable Polymers for Biomedical Uses", Progress in Polymer Science, 1994, 19, 633]. Biodegradation of inorganic matter is defined as potential existence for resorption and/or degradation of the material and its subsequent elimination from the body or its further use to form new tissue. Latter either proceeds via dissolution and usage of released ions for direct precipitation or via transformation from one inorganic synthetic phase (e.g. ATCP) to another physiologically favored phase (e.g. hydroxyapatite) or via seeded growth. Both biodegradable polymers and inorganic matter (ceramics) typically fulfill the requirements of DIN EN ISO 10993. In particular, detailed procedures to qualitatively and quantitatively determine degradation products of polymers [DIN EN ISO 10993-13] and ceramics [DIN EN ISO 10993-14] are given.

The term "nanoparticles" is known in the field. Nanoparticles may be characterized by its mean primary particle size or by its specific surface area ("SSA"). Typically, nanoparticles as used in this invention have a mean primary particle size $d_{p,\ mean}$ of below 500 nm, preferably below 100 nm, if calculated according to the formula $d_{p,\ mean}=6/(\rho*SSA)$, where $\rho$ is the density of the powder and SSA is the specific surface area obtained by nitrogen adsorption using the Brunauer-Emmett-Teller method.

The term "bone defects" describes any physical damage of bone of the human being or an animal. It includes injuries, bone loss due to a disease, fractures and the like.

The invention will be better understood and objects other than those set forth above will become apparent when consideration is given to the following detailed description thereof. Such description makes reference to the annexed figures, wherein.

Figure 3:
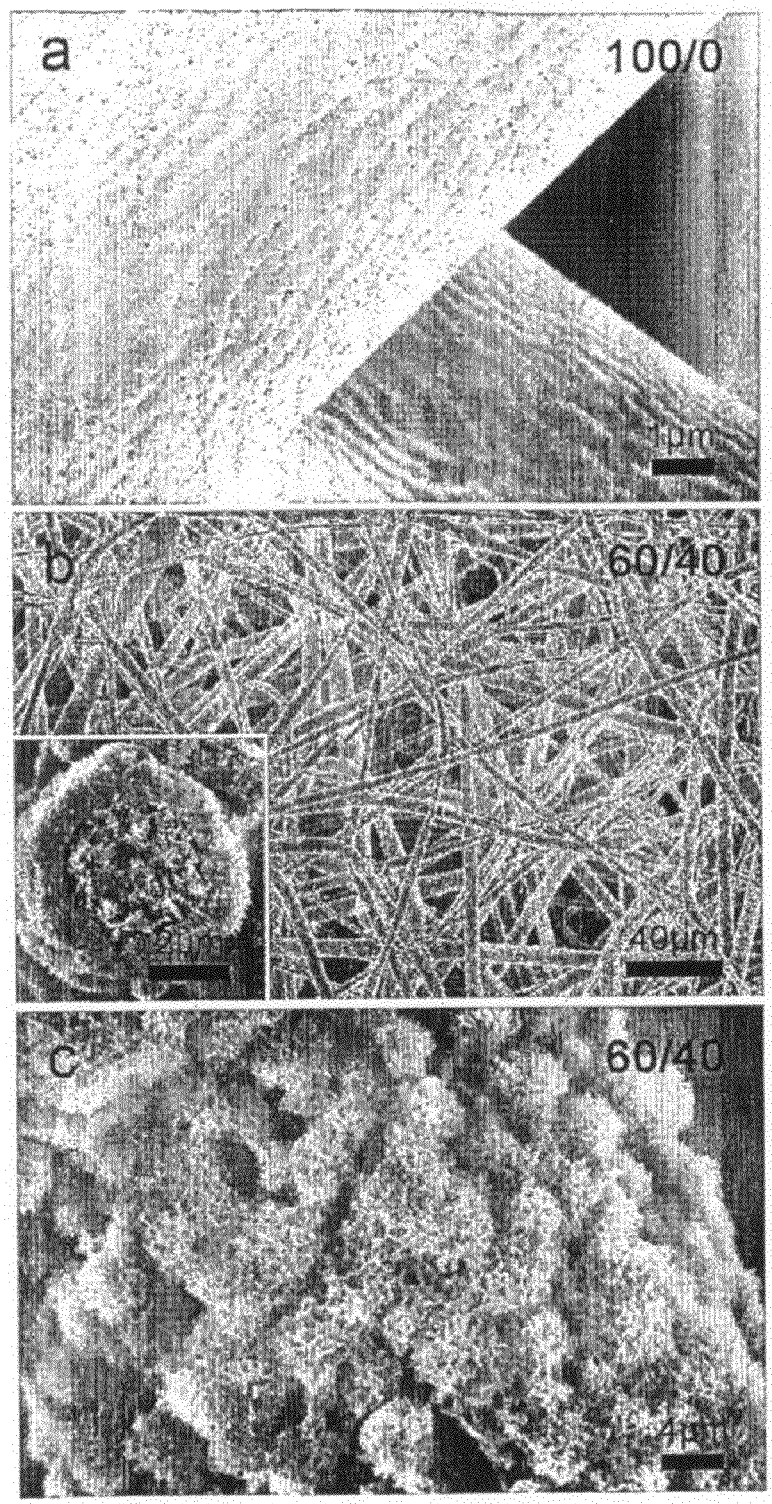

FIG. 3 shows SEM images after 45 h immersion in SBF for pure PLGA (a) and PLGA/TCP 60:40 (b,c). The cross section of a PLGA/ATCP fiber shows a HAp layer of ~1 μm (b, inset). The deposition of nano-featured HAp showing a cauliflower-like morphology occurs only for ATCP doped PLGA (c).

Figure 4:
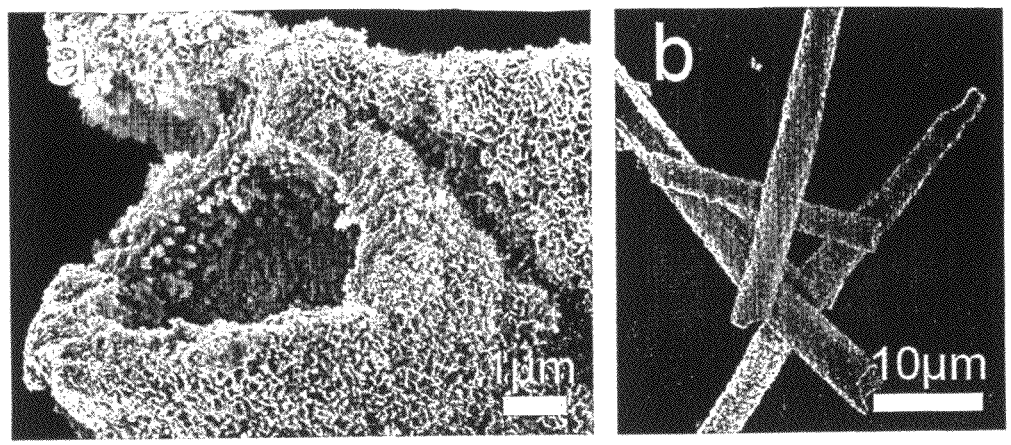
Figure 5:
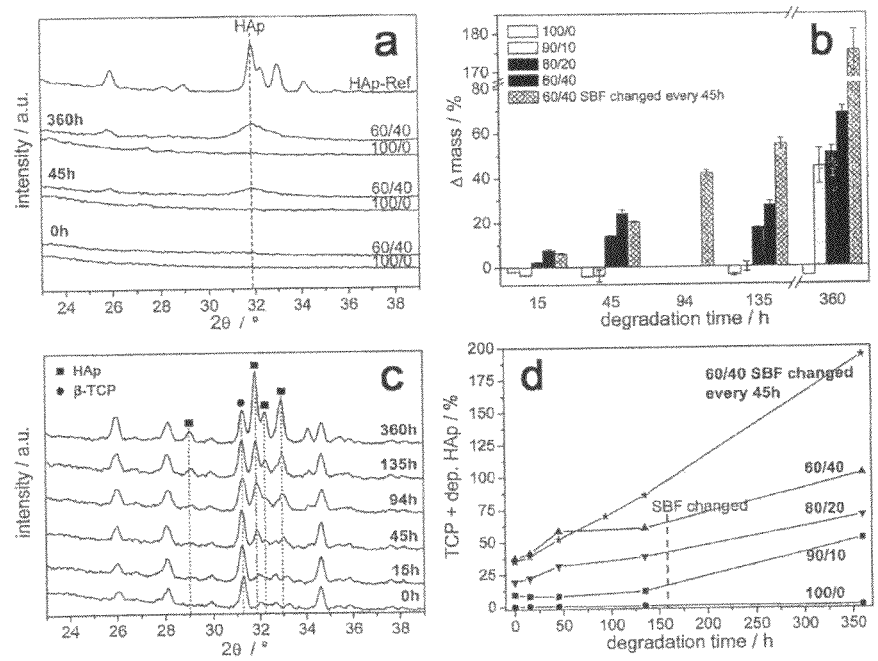

FIG. 4 shows SEM of extracted PLGA/TCP 60:40 hydroxyapatite tubes after 45 h immersion in SBF;

FIG. 5 shows X-ray powder diffraction patterns of dried pure PLGA and nanocomposite samples after different degradation times revealing the formation of nanocrystalline HAp for ATCP doped samples (a). Change in mass of different PLGA/ATCP nanocomposites in percent as a function of immersion hours in SBF, which was changed once after 160 h. In an additional experiment of sample PLGA/ATCP 60:40 the SBF was changed every 45 h (b). X-ray powder diffraction patterns of PLGA/ATCP 60:40 (SBF changed every 45 h) after sintering at 1000° C. shows the increasing ratio of distinct signals characteristic for β-TCP and HAp (c). Inorganic contents in percent after degradation related to the weight before degradation (d).

Figure 6:
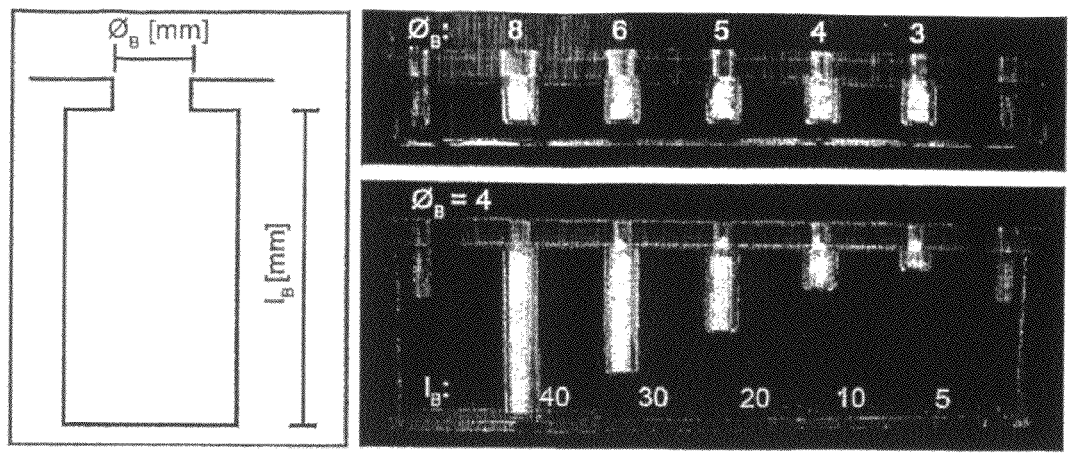

FIG. 6 shows the simulation of a bone defect site with hindered accessibility. Defects with different opening diameters $\varnothing_B$ and depths $l_B$ can be completely filled with the prepared bone cotton.

Figure 7:
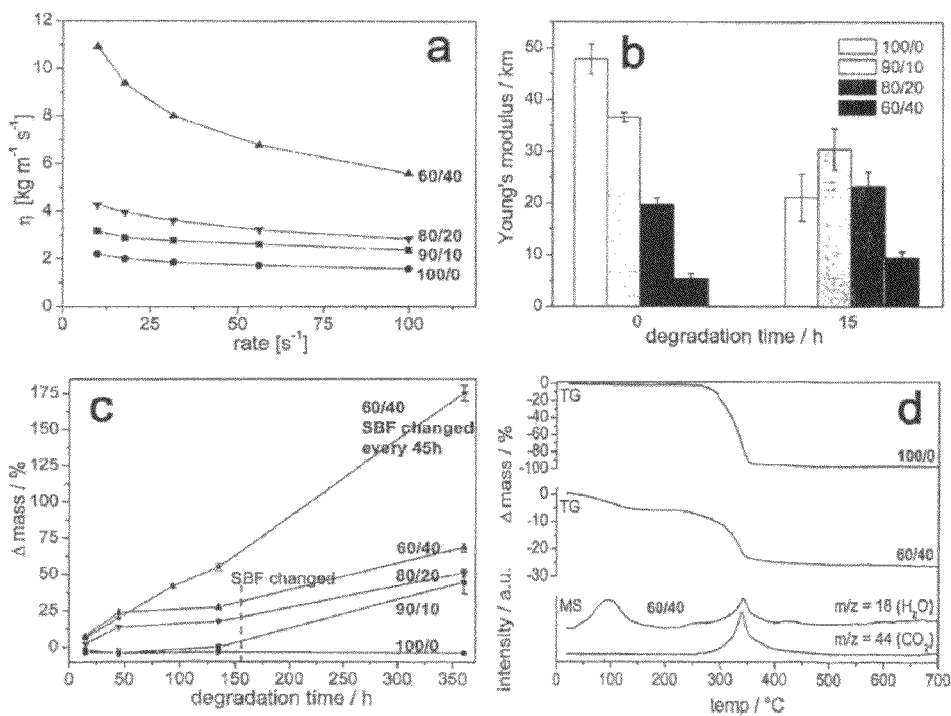

FIG. 7 shows viscosities of the different PLGA/ATCP electrospinning solutions as a function of the shear rate (a). Young's modulus of undoped and ATCP doped PLGA as a function of degradation time (b). Change in mass of different PLGA/ATCP nanocomposites in percent as a function of immersion hours in SBF (c). Thermo-gravimetric analysis coupled with mass spectroscopy showing the release of about 5 wt % physisorbed water below 150° C. for ATCP doped PLGA after 360 h degradation (d).

In a first aspect, the invention relates to a pharmaceutical composition in the form of fibers comprising one or more biodegradable polymers and one or more biodegradable inorganic nanoparticles having a mean primary particle size below 500 nm and optionally pharmaceutically active ingredients and/or proteins.

Biodegradable polymers: In the context of this invention, a wide variety of biodegradable polymers, derived from artificial or natural sources, may be used. To choose the appropriate polymer; the degradation time and manufacturing properties will be considered. Such polymers are commercially available or may be manufactured according to known procedures. Examples of suitable polymers (homopolymers, copolymers and its blends) can be divided into two subsections as described in (Hayashi, T., "Biodegradable Polymers for Biomedical Uses", Progress in Polymer Science, 1994, 19, 633):

i) Enzymatically degradable polymers: This section includes natural polypeptides (e.g. collagen, gelatin, albumin, fibrinogen), synthetic polypeptides (e.g. poly(L-glutamic acid), poly-L-lysin, poly-L-leucine, poly-L-alanine), polysaccharides (e.g. amylase, Hydroxyethylstarch, dextran, alginic acid, chitin, chitosan), and biopolyesters (e.g. poly(β-hydroxyalkanoate).

ii) Nonenzymatically degradable polymers: Including poly (α-hydroxy acids) (e.g. poly-(glycolide), poly-(lactide), poly (α-malic acid)), poly(ω-hydroxyl acids) (e.g. poly(epsilon-caprolactone), poly(β-hydroxyal-kanoate)), poly(ortho esters), polyanhydride, polycarbonate (e.g. poly(1,3-dioxan-2-one)), inorganic polymers (e.g. polyphosphazene). Particular suitable are polymers or copolymers of glycolic, lactic acid such as PLGA; e.g. PLGA 85/15; PLGA 80/20; PLGA 60/40. (Co-)Polymers of lactic acid may be manufactured of D-, L- or DL lactic acid.

Biodegradable inorganic nanoparticles: In the context of this invention, a wide variety of biodegradable inorganic nanoparticles may be used. Typically, such inorganic nanoparticles comprise a salt of calcium. Suitable materials for such inorganic nanoparticles are XRD-amorphous calcium phosphates, in particular with a calcium to phosphorous ratio between 1.5 and 2.0, alpha-tricalcium phosphate, beta-tricalcium phosphate, hydroxyapatite, calcium deficient hydroxyapatite as described in [K. ISHIKAWA, P. DUCHEYNE, S. RADIN, Determination of the Ca/P ratio in calcium-deficient hydroxyapatite using X-ray diffraction analysis, Journal of Materials Science Materials in Medicine, 4 (1993) 105-168], carbonated hydroxyapatite, calcium-deficient carbonated hydroxyapatite, fluorine substituted hydroxyapatite (Ca10(PO4)6(OH)xF(2−x), where 0≦x<2), bioactive glasses and glass-ceramics as described in ["Biomaterials Science. *An Introduction to Materials in Medicine*.", Eds. B. D. Ratner, A. S. Hoffman, F. J. Schoen, and J. E. Lemons, Elsevier, Amsterdam 2004], calcium carbonate, calcium sulfate, or calcium sulfate-hydrate which may be further modified as explained in more detail below. A preferred material is tricalcium phosphate (TCP), in particular amorphous tricalcium phosphate (ATCP). TCP is considered amorphous, if no, or essentially no, X-ray diffraction signals are distinguishable (thus, no periodic ordering of the ions in the crystal). Further, amorphous TCP has the highest free enthalpy of formation when compared to other crystal modifications. The manufacture of nanoparticles as described herein is known. They are accessible e.g. by Flame Spray Pyrolysis ("FSP"), methods for manufacturing are described e.g. in [6].

Pharmaceutically active ingredients ("a.i."): The fibers or fibrous webs may be coated/soaked with one or more a.i. Suitable a.i.'s are selected from the group consisting of antimicrobiotic, antifungal, anti-inflammatory and immunosuppressive active ingredients. Such a.i.'s are known to the skilled person and may be identified in the "Orange Book" [Approved Drug Products with Therapeutic Health and Human Services, 2006]. Here, the fibrous web keeps a specific medication in place and the minimal amount of composite helps to avoid unwanted side-effects. Pouring the medication as a liquid into the target site would result in liquid spreading out in an uncontrolled manner. In a preferred embodiment, fibrous webs are soaked with one or more a.i.'s.

Proteins: The fibers or fibrous webs may be coated/soaked with one or more proteins. Suitable proteins support bone healing (such as the bone morphogenic protein "BMP") and/or influence the differenciation of bone marrow stem cells to osteoclasts/osteoblasts. In a preferred embodiment, fibrous webs are soaked with one or more proteins.

Body fluids: The fibers or fibrous webs may be coated/soaked with one or more body fluids. Suitable body fluids include blood, bone marrow. It is believed that this improves handling properties and wound healing.

In an advantageous embodiment, the biodegradable inorganic nanoparticles essentially consist of XRD-amorphous calcium phosphates, in particular with a calcium to phosphorous ratio between 1.5 and 2.0, alpha-tricalcium phosphate, beta-tricalcium phosphate, hydroxyapatite, calcium deficient hydroxyapatite, carbonated hydroxyapatite, calcium-deficient carbonated hydroxyapatite, fluorine substituted hydroxyapatite (Ca10(PO4)6(OH)xF(2−x), where 0≦x<2), bioactive glasses and glass-ceramics, calcium carbonate, calcium sulfate or calcium sulfate-hydrate, wherein some or all, preferably up to 20%, of the Ca-ions are stoichiometrically replaced by one or more elements selected from the group comprising strontium, magnesium, sodium, potassium, bismuth, barium, gadolinium, europium, holmium, neodymium or praseodymium, preferably strontium, magnesium, sodium, potassium, bismuth.

In a further advantageous embodiment, the biodegradable inorganic nanoparticles essentially consist of XRD-amorphous calcium phosphates, in particular with a calcium to phosphorous ratio between 1.5 and 2.0, alpha-tricalcium phosphate, beta-tricalcium phosphate, hydroxyapatite, calcium deficient hydroxyapatite, carbonated hydroxyapatite, calcium-deficient carbonated hydroxyapatite, fluorine substituted hydroxyapatite (Ca10(PO4)6(OH)xF(2−x), where $0 \leq x < 2$), bioactive glasses and glass-ceramics, calcium carbonate, calcium sulfate or calcium sulfate-hydrate wherein up to 0.5 mass-% of the Ca-ions are replaced by silver which is present as Ag+.

In a further advantageous embodiment, the biodegradable inorganic nanoparticles essentially consist of XRD-amorphous calcium phosphates, in particular with a calcium to phosphorous ratio between 1.5 and 2.0, alpha-tricalcium phosphate, beta-tricalcium phosphate, hydroxyapatite, calcium deficient hydroxyapatite, carbonated hydroxyapatite, calcium-deficient carbonated hydroxyapatite, fluorine substituted hydroxyapatite (Ca10(PO4)6(OH)xF(2−x), where $0 \leq x < 2$), bioactive glasses and glass-ceramics, calcium carbonate, calcium sulfate or calcium sulfate-hydrate wherein up to 0.5 mass-% of the Ca-ions are replaced by silver which is present as Ag+ and up to 10 mass-% of Ag which is deposited on top of the surface as metallic particles having a mean primary particle size below 10 nm. The manufacture of such nanoparticles is known and described e.g. in WO2005087660

The fibres according to this invention may contain 1 to 80 mass-% nanoparticles, preferably 5 to 40 mass-% nanoparticles. Further, the fibres may contain up to 5 mass-% of pharmaceutically active ingredient(s) and/or up to 1 mass-% protein(s).

Further, the invention relates to an implant material, essentially consisting of a pharmaceutical composition in the form of fibres as disclosed herein.

Homogeneity: In an advantageous embodiment, the invention relates to a pharmaceutical composition as described herein wherein the biodegradable inorganic nanoparticles are homogeneously distributed within the biodegradable polymer. Pharmaceutical compositions as described herein may be characterized as homogeneous or inhomogeneous. Inhomogeneous Pharmaceutical compositions are characterized by the presence of ceramic-rich and polymer-rich areas. If the concentration of the constituents is measured by chemical or physical analysis (e.g. energy dispersive X-ray analysis in a transmission electron microscope) along an arbitrarily line crossing within (not through a pore) the composite material, large deviations (over +/−40% of the mean mass based composition of the material) in composition are found at a length scale above 2 micrometer. Most of these inhomogeneous materials are white (light scatters on the inhomogeneities), grainy and supplied as granulate with strong composition gradients within the individual particles. Homogeneous pharmaceutical compositions consist of a smooth composition profile when using a similar analytical technique as outlined above (spatial resolution of 1 micrometer, variations of less than 30% of the mean mass-based composition) if crossing the composition along an arbitrary line. Such materials are easier characterized and provide an uniform chemical and physical set of properties. Only minor changes in composition are found within a single granulate or fiber of such a material. More specifically, the mass content (in weight-percent; measured as mass of the major constituent over mass total) over the cross-section of such a material does not deviate by more than 20% in mass from the center to the edge of the cross-section when applying a spatial resolution of 1 micrometer. The procedure does not consider to cross an air filled pore or core/shell geometries prepared from materials with different compositions, e.g. the line of observation stays within the composite material originated from the same precursor composite material.

Bulk Density: In an advantageous embodiment, the invention relates to fibrous webs, essentially consisting of fibers as described herein, having a bulk density between 0.001-1.7 g/cm3, preferably between 0.01 and 0.5 g/cm3. The bulk density is the mass of a sample divided by its volume. Implant materials for load-bearing implants are generally dense (density over 1 g/cm$^3$) as they have to sustain strong forces. Implant materials for non-load bearing defects or for bone growth guidance can be of low density. It is believed that it is preferable to introduce as little as possible alien material into a body. Thus, the fibrous webs according to this invention offer the possibility to introduce less alien material into the living body when compared with standard surgery methods.

Flexibility: In an advantageous embodiment, the invention relates to a pharmaceutical composition as described herein which is flexible and/or compressible. The ability to give a material a different shape by merely applying a force on the required direction may be defined as flexibility. Warm candle wax, cotton wool, pottery earth are examples from everyday live that represent flexible materials. Flexibility may be quantified by comparing the change in a characteristic length of a piece of material under a given force or pressure.

Compressibility: In an advantageous embodiment, the invention relates to a pharmaceutical composition as described which is compressible. Compressibility is the volume contraction upon application of pressure. Among the above everyday examples, warm candle wax and pottery earth are almost incompressible while cotton wool can easily be compressed.

Elasticity: In an advantageous embodiment, the invention relates to a pharmaceutical composition as described which is elastic. After compression, a specific material may either stay in the new shape if the force is removed, or, it may partially or fully regain its original shape. A rubber ball is very elastic while pottery earth yields to a force and stays in the new shape.

In a further embodiment, the invention relates to an adaptive implant, essentially consisting of fibers as described herein. An implant is regarded adaptive, if it is flexible and/or compressible and/or elastic. Such adaptive implants are convenient for handling. As a consequence, such implants may reduce the time of operation (as discussed above) and are highly desirable.

Further, the fibrous web as disclosed herein provide an implant substitute that is easily removed if needed, e.g. for correction. Even a most skillful surgeon will often require re-adjusting his/her implant in a site of operation. Or, removal of the implant is becoming necessary during an operation as a specific incident triggers a change in plan of the operation. A fibrous web implant can be easily removed from a site of implantation as the material is well connected together. Its property (fibers) allow easy removal from a site of insertion, often, more than 98% of the mass of the implant are removed in a single movement, which is regarded a significant advantage over the known materials.

In a second aspect, the invention relates to the manufacture of a pharmaceutical composition as described herein comprising the steps of—process (A)—i) dissolving one or more biodegradable polymers in a solvent or melting one or more biodegradable polymers; ii) optionally dissolving additives in the solution or melt; iii) dispersing one or more biodegradable inorganic nanoparticles in the obtained liquid; iv) optionally dissolving/dispersing pharmaceutically active ingredients/proteins and v) subjecting the obtained composition to a spinning process or, —process (B) i) optionally dissolving additives in a solvent; ii) dispersing one or more biodegradable inorganic nanoparticles in the obtained solution iii) dissolving one or more biodegradable polymers in the obtained dispersion; iv) optionally dissolving/dispersing pharmaceutically active ingredients/proteins and v) subjecting the obtained composition to a spinning process.

The individual steps, parameters and components are explained below.

The spinning process used according to this invention may be any spinning process known in the field which produces fibres of the desired size and is compatible to the materials employed (in particular operates at low temperatures) and includes solvent based spinning processes as well as spinning of a melt. Suitable processes include wet spinning, dry spinning, melt spinning, gel spinning, phase separation spinning, flash spinning, meltblowing, electrostatic spinning as detailed in [Fundamentals of fibre formation: the science of fibre spinning and drawing/Andrzej Ziabicki. —London a.o.: Wiley, 1976.] and [Nonwoven fabrics: raw materials, manufacture, applications, characteristics, testing processes/ed. by W. Albrecht et al. —Weinheim Wiley-VCH, 2003.]. Fibers may also be produced in a bicomponent and biconstituent form (e.g. core/shell geometry) with the mentioned processes as described in [Fundamentals of fibre formation: the science of fibre spinning and drawing/Andrzej Ziabicki. —London a.o.: Wiley, 1976.].

In an advantageous embodiment, the spinning process is centrifugal spinning.

In a further advantageous embodiment, the spinning process is electro spinning. Electrospinning is known in the field and regarded a suitable tool for the preparation of open structured, highly accessible networks of polymer fibers. The process is already used to synthesize materials for various applications, such as in reinforcement, filtration, medical prostheses engineering, wound dressings and tissue engineering.

To dissolve the biodegradable polymer any suitable solvent may be used. Such solvent may not react with any of the components and should be easily removed prior to the use of the fibres obtained. Examples of suitable solvents include haloalkahes (such as CHCl3); alcohols (such as EtOH; i-PrOH); esters (such as EtOAc); ketones (such as acetone) and ethers (such as THF) and their mixtures.

Optionally, one or more additives may be employed to facilitate the manufacturing. Such additives and their handling are known in the field. Typical additives are biocompatible surfactants, e.g. selected from the class of sugar derivatives. Such additives may be added at any suitable step prior to the spinning process.

Further the spun fibers may be subsequently processed to a yarn by conventional manufacturing methods which are known in the field such as different spinning processes and air texturizing. The obtained yarn consisting of one or more fiber/s (so-called plies) can be used as is in surgery e.g. for sewing. Optionally the yarn may be further woven to a 3 dimensional structure (woven fabric) before application serving e.g. as structure guidance for tissue regeneration. Processes for producing woven fabrics are known in the field. Accordingly, yarns and woven fabrics as well as their manufacturing and use are also subject to the present invention.

The processes for coating fibers, fibrous webs, yarns and woven fabrics with an a.i. or protein are known in the field and applicable for the materials according to this invention. The coating may either be applied directly in the fiber production process (e.g by spinning a core/shell structure with corresponding precursors) or after the spinning process. The subsequent coating includes but is not restricted to dip coating, flow coating, dip-spin coating, and spray coating as described in [Industrial Painting & Powdercoating: Principles and Practices, 3rd Ed., Norman R. Roobol, 2003, Hanser Gardner].

The process for dip coating fibrous webs with an a.i., protein or body fluid is known in the field. It includes the step of dipping the fibrous web in a solution containing an effective amount of the a.i., protein or body fluid and a suitable diluent (such as sterile water, synthetic body fluid and the like) and optionally drying the obtained soaked fibrous web.

Further, the invention relates to material obtained by a process as described herein.

In a third aspect, the invention relates to the use of fibers/fibrous webs as described herein in various applications. Fibrous webs according to the invention may be used in a large variety of applications as degradable implant material/for the treatment of bone defects. This includes the use as i) filler material in dental- or skeleton-related applications and ii) the use in the field of tissue engineering, e.g. as cartilage substitute/repair of cartilage defects or for bone replacement, regeneration/reinforcement. Advantageously, the fibrous webs may be used in the treatment of non-load bearing defects. Detailed examples of uses are given below:

A) Use of the fibrous web in the sinuslift with lateral and crestal approach. Here, the fibrous web acts as a filler material for coagulum stabilization, space maintenance and may be osteoconductive and/or -inductive (in particular, if bioactive material is incorporated). In the case of the (modified) Summers technique, it also acts as a cushion to prevent Schneiderian membrane perforation or damage. More details on the procedure are provided in Emmerich 2005, Garg 1999 and Lazzara 1996 the content of which is incorporated by reference.

B) Use of the fibrous web in guided bone regeneration (GBR) procedures such as the two-stage management of deficient bone, i.e. lateral and vertical bone augmentation. The fibrous web according to this invention can also be applied using minimal invasive approaches. Due to its flexibility and compressibility, a piece of fibrous web can be compacted and inserted into a site through a small opening. More specifically, the diameter of the opening for insertion may be much smaller than the actual diameter of the defect. Typical ranges can be a five times smaller opening for insertion if compared to the diameter of a filling. In short, a muco-periostal flap or rather pocket is raised by a small incision in the area to augment without hampering the vascularization of the soft tissue. The small damage in the soft tissue strongly supports rapid healing. The material is inserted until the desired bone contour is achieved. The incision is closed by sutures and the periosteum may act as a natural membrane to allow for bone regeneration underneath. Here, if the periosteum is used as membrane, the bone guidance comes from the periosteum and strongly supports the regeneration process. The fibrous web can also be applied simultaneously during one-stage implantation procedures to augment bone or in the treatment of periimplantitis. The fibrous web can be used with or without an additional occlusive membrane. More details on the procedure are provided in Esposit 2006 and Hammerle 2002, the content of which is incorporated by reference.

C) Use of the fibrous web as a socket preservation material, which is implanted immediately after tooth extraction in the extraction socket. Here, the fibrous material acts as a coagulum stabilizer and supports the bony walls (especially at the buccal aspect). A preservation especially of the bundle bone, which normally resorbs, is highly desired and may be achieved by mechanical and chemical means. As a consequence, the soft tissues are maintained accordingly. Hard and soft tissue management may thus lead to improved implantation protocols. More details on the procedure are provided in Fiorellini 2003 and Schmidlin 2004, the content of which is incorporated by reference.

D) Use of the fibrous web in guided tissue regeneration (GTR) procedures in periodontal defects, i.e. vertical (or even horizontal) and furcation defects. The fibrous web can be used to fill the defect areas with or without an additional occlusive membrane (see also subsection B) above). Detailed procedures may be found in Needleman 2006, Novaes 2005, Murphy 2003, the content of which is incorporated by reference.

E) Use of the fibrous web in the closure of oro-antral communications (acute or chronic). The fibrous web is inserted in the defect and acts as a plug to close the communication. In contrast to particle grafts, a transposition into the sinus can be avoided. Particulate graft materials may be used additionally. The procedure is outlined in Mehra 2004 and Thoma 2006, the content of which is incorporated by reference.

F) Use of the fibrous web as a scaffold for dentin regeneration. The architecture can mimic the natural dentin. The fibrous web may allow dentinoblasts and other tooth-deriving cells or stem cells to adhere, differenciate and form new dentin, optionally with the addition of growth factors or promoters to the fibrous web. Details on the procedure may be found in Goldberg 2006 and He 2006, the content of which is incorporated by reference.

G) Use of fibrous web for pulp capping procedures. The fibrous web can be applied on perforated (sterile and infected) pulps. The material stops bleeding and allows for dentin bridging at the pulpal side. On top of the material, compatible restorative materials are applied to close the tooth defect and prevent leakage and infection and restore tooth function. Details on the pulp regeneration may be found in Nakashima 2005, the content of which is incorporated by reference.

H) Use of the fibrous web for the filling of bony defects in the field of dental and oral and maxillofacial surgery. As an example, the filling of the bone defects after root-end resection may be mentioned.

Thus, the present invention also relates to a method of treatment of bone defects comprising the step of applying an effective amount of fibrous web to the site of operation.

The fibrous webs, also referred to as bone-wool, is flexible over multiple length of its original shape and it can be formed to fluffy balls, strings, loose nets, sticks or other shapes right at the operation. Its properties allow the surgeon to manipulate bone-wool by his or her fingers, not requiring additional heavy duty mechanical tools. The density of bone wool can be adjusted by compaction either before introduction into a defect, gap or hole, or, by modifying the amount of bone wool inserted in the volume of a defect, gap or hole.

In a further embodiment, the invention relates to the use of patient-own bone marrow together with fibrous webs as described herein as a partial autograft. Here, the advantageous properties of the nanoparticle containing fibrous web allow accommodating bone marrow from the patient. The release of calcium and phosphate from the bone wool supports the self-regeneration of the bone tissue at the site of defect, fracture or correction. Little alien material is used to keep the bone marrow in place within a given specific defect geometry. Again, the low density of the material is a significant advantage.

In a further embodiment, the invention relates to the use of fibrous webs as disclosed herein as a vehicle for delivering pharmaceutically active ingredients ("a.i.'s") to the site of operation. This provides an easy and safe way of applying medication to the specific site of the body where this medication is needed.

Thus, the fibrous web may be regarded as a carrier for one or more a.i.'s. The invention also relates to the use of fibrous webs, for the manufacture of a medicament for the treatment of bone defects. The invention also relates to a method of treatment of bone defects comprising the step of applying a fibrous web, said fibrous web being soaked/coated with an effective amount of one or more active ingredients, to a subject in need of such treatment. The invention also relates to a composition comprising a fibrous web, said fibrous web being soaked/coated with one or more for use as a pharmaceutical.

In a specific embodiment, ATCP nanoparticles are prepared by flame spray synthesis and incorporated in biodegradable PLGA at weight ratios up to 40%. Randomly oriented, homogeneous fibers with a diameter ranging from 5 to 10 um were produced by electrospinning. The fibrous webs obtained are in vitro degraded in simulated body fluid and the bioactivity is investigated in terms of hydroxyapatite deposition. The formation of a hydroxyapatite layer in the micrometer range on the surface of the fibers is observed for such fibrous webs (while webs without ATCP nanoparticles do not show such an effect). It was found that the process of deposition was increasing with both immersion time and nanoparticle content while it was found to be limited by ion supply from SBF following first order kinetics. Therefore the composition of the fibrous webs allows thoroughly control on the rate of apatite formation. For example, a loading of 40 wt % ATOP resulted in a triplication of the initial mass after 15 days of immersion, which is attributed to the deposition of bone-like material (i.e. hydroxyapatite).

The following examples are intended to illustrate the invention, with no intention to limit the invention to the specific examples.

1. Preparation of ATOP particles: Amorphous tricalcium phosphate nanoparticles (ATCP, $Ca_3(PO_4)_2$) were prepared by flame spray pyrolysis using calcium hydroxide (Riedel de Haen, Ph. Eur.) dissolved in 2-ethylhexanoic acid (Soctech, Romania) and tributyl phosphate (97%, Aldrich) as precursors [6]. The liquid mixture was diluted with xylene (2:1 vol/vol) and fed through a capillary (diameter 0.4 mm) into a methane/oxygen flame at a rate of 5 ml/min. Oxygen (5 L/min, 99.8%, Pan Gas) was used to disperse the liquid leaving the capillary and resulted in a burning spray of about 10 cm height. A more detailed view on the nanoparticle formation may be found in [9]. The as-formed particles (production rate: 8 g h−1) were collected on a glass fiber filter (Whatmann GF/A, 25.7 cm diameter), placed on a cylinder mounted above the flame, by the aid of a vacuum pump (Busch Seco SV 1040 C). The resulting ATCP nanoparticles were sieved (450 μm mesh) after collection.

2. Analysis of ATCP particles: The specific surface area (SSA) of the ATCP powder was measured by nitrogen adsorption at 77 K (Tristar, Micromeritics) according to the Brunauer-Emmett-Teller (BET) method after outgasing at 150° C. for 1 h. The primary particle diameter was calculated according to dBET=6/(pATCP·SSA) assuming spherical particles. Hydrodynamic particle size distributions were measured on an X-ray disk centrifuge (BI-XDC, Brookhaven Instruments) [10] using 1.5% (wt/vol) of powder in absolute ethanol (Fluka) and the mean particle diameter was denoted as dXRD. Prior to analysis the powder was dispersed by ultrasonication (UP400S, 24 kHz, Hielscher GmbH) at 200 W for 5 min. The average number of primary particles per aggregate (np) was roughly estimated using the fractal scaling relationship (np=[dc/dp]D) applying dBET as primary particle diameter (dp), dXDC as collision diameter (dc) and a constant fractal dimension (D) of 1.8 consistent with theory for nanoparticle formation in flames [11]. For Fourier transform infrared (FTIR) spectroscopy, 1 wt % of powder was mixed with KBr (Fluka, puriss) and examined on a Tensor 27 spectrometer (Bruker Optics, 4000 cm$^{-1}$<λ<400 cm$^{-1}$, 16 scans, 4 cm$^{-1}$ resolution) equipped with a diffusive reflectance accessory (DiffusIR™, Pike Technologies). Transmission electron microscopy (TEM) images were recorded on a CM30 ST (Philips, LaB6 cathode, operated at 300 kV, point resolution ~4 Å). Particles were deposited onto a carbon foil supported on a copper grid.

3. Scaffold preparation: Clinically approved poly(lactide-co-glycolide) (PLGA) with a copolymer ratio of 85:15 (Resomer® Sample MD Type RG) was purchased from Boehringer Ingelheim with a weight and number average molecular weight of 380'300 g/mol and 181'900 g/mol, respectively. Randomly oriented PLGA/ATCP fibers were fabricated in different weight ratios (100:0, 90:10, 80:20 and 60:40) by the electrospinning process [5]. Each electrospinning solution was prepared with a concentration of 8 wt % PLGA in chloroform (Riedel de Haen, Ph. Eur.) containing 5 wt % Tween20 (Fluka, Ph. Eur.) referred to the polymer. For the preparation of the electrospinning solution, corresponding amounts of ATCP nanoparticles were first dispersed in a chloroform/Tween20 parent solution using an ultrasonic processor (UP400S, 24 kHz, Hielscher GmbH) at 320 W for 5 min applying pulsed intervals to allow for relaxation of the particles. PLGA was subsequently added and dissolved for 15 h by magnetic stirring. The viscosity of the resulting mixture was measured with a rheometer (Rheometric Scientific, cone plate 50 mm, shear rate 10-100 s$^{-1}$). The electrospinning was done feeding the solutions through a capillary (inner diameter 1.0 mm) using a syringe pump (Seringue, Bioblock Scientific). The feeding rate was set to 2 ml/h for PLGA/ATCP 60:40 and 4 ml/h for all other solutions. A high voltage supply (Glassman High Voltage) was used to apply voltages of 20 kV to the needle tip which was kept in a chloroform/air stream (1 l/min) by a concentrically mounted sheath tube [12]. A positively charged jet was formed from the Taylor cone and was sprayed onto a rotating (130 rpm) collection tube covered by aluminum foil. The distance between the needle tip and the collection tube (diameter 8 cm) was kept at 10 cm for PLGA/TCP 60:40 and 20 cm for all other samples. The as-spun scaffold was dried and stored under vacuum at room temperature.

4. Scaffold analysis: The morphology of the electrospun fibres was characterized using scanning electron microscopy (SEM; Hitachi S-900) at a voltage of 3 kV after sputtering the samples with platinum (4 nm, Bal-Tec SCD 050). The porosities of the scaffolds were calculated according to $\epsilon$=(Vtot−Vsolid)/Vtot, whereas the total volume (Vtot) was determined from the base area of the sample and its thickness as measured by SEM. The solid volume (Vsolid) is given by the sample mass and its density. X-ray diffraction (XRD) patterns were collected on a Stoe STADI-P2 (Ge monochromator, CuKα1, PSD detector). Mechanical properties were obtained by tensile tests on an Instron 4411 (Instron Co.). Five dog-bones (stressed length 12.6 mm, width 2 mm) of each scaffold were taken and tested at ambient conditions with a crosshead speed of 12.6 mm min$^{-1}$. Thermo-gravimetric analysis (TGA/SDTA851e, Mettler Toledo) coupled with mass spectroscopy (MS, Pfeiffer OmniStar™) allowed for determination of the inorganic fraction as well as the simultaneous detection of desorbing water and carbon dioxide by heating the samples up to 700° C. at a heating rate of 5° C. min$^{-1}$. Routinely, the inorganic content in the scaffolds was determined by heating samples up to 700° C. for 30 minutes. In order to study the hydrophilicity of pure PLGA and PLGA/ATCP composite materials, films with a thickness of 100 μm were prepared by solvent casting from the electrospinning solution and the contact angle was measured (Goniometer, ramé-hart inc).

5. In vitro degradation experiments: Scaffolds were cut into rectangles (70×10 mm$^2$) for in vitro degradation tests. After UV-sterilization (50 W/m$^2$, 2 hours) [13], the samples were placed in bottles containing 500 ml simulated body fluid (SBF, pH 7.4) and incubated at 37° C. for different time intervals (15 h, 45 h, 135 h and 360 h). SBF was prepared according to Oyane et al. [14] and sterile-filtered through a pre-sterilized filter unit (Millipore, 0.22 μm). In a typical degradation experiment the SBF was changed after 160 h. In order to guarantee a constant liquid composition the SBF was changed every 45 h in a second experiment using the scaffold PLGA/ATCP 60:40. Each degradation experiment was carried out using four samples (weight before degradation, W0) from the same scaffold. After each degradation period, the samples were washed with Millipore water, dried for 15 h in an evacuated exsiccator at room temperature and weighted (dry weight, Wd). The percentage weight gain (Δmass %) of the samples was calculated from the weight before and after degradation according to Δmass %=(Wd−W0)/W0·100. Gel permeation chromatography (GPC, Viscotek TDA) using tetrahydrofuran/toluene (95:5) as eluting solvent was performed in order to study the degradation of the PLGA during the experiment. Before GPC measurement the particle containing scaffolds were dissolved in chloroform (Riedel de Haen, Ph. Eur.) and centrifuged. The supernatant was collected and examined by GPC.

Figure 1:
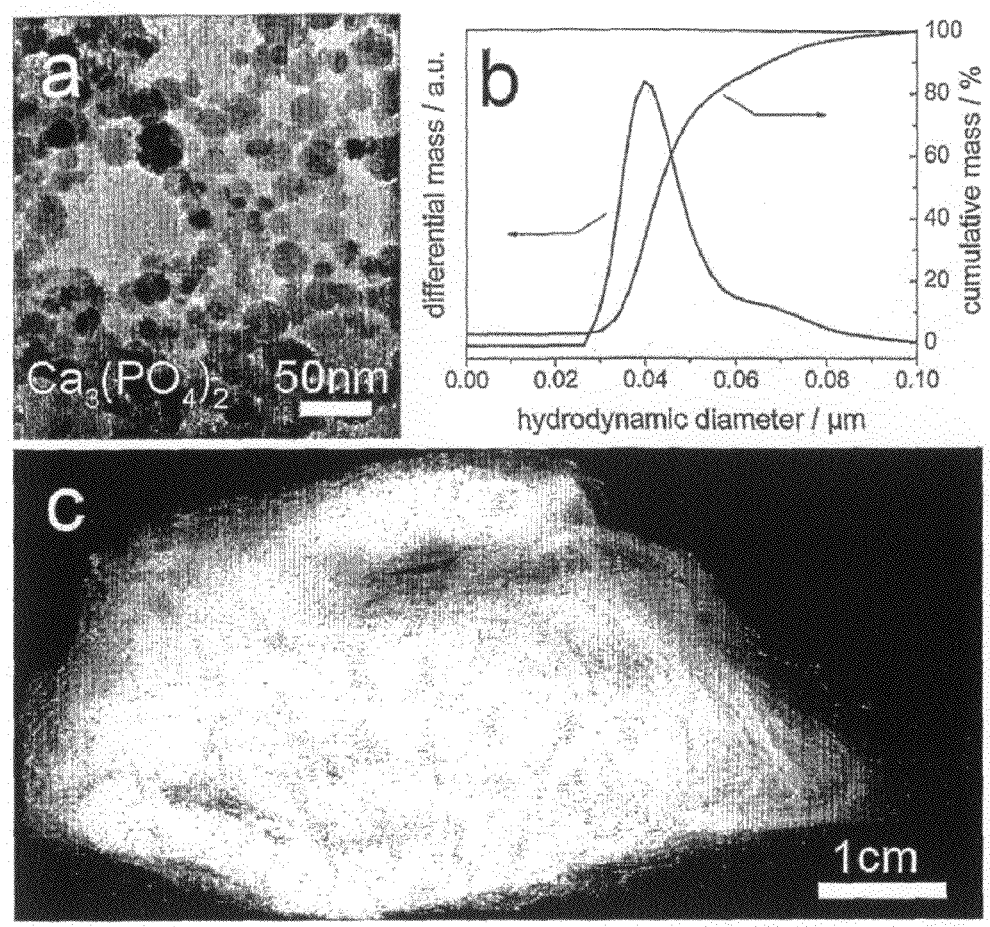
FIG. 1 shows a transmission electron microscopy image of as-prepared amorphous tricalcium phosphate (ATCP) nanoparticles (a); the corresponding hydrodynamic particle size distributions of ATCP measured by X-ray disk centrifugation (b); a photograph of as-electrospun PLGA/ATCP scaffold prepared into cotton-like biomaterial (c).

6. ATCP characterization: Production of ATCP particles by flame spray synthesis yielded spherical, amorphous and highly agglomerated tricalcium phosphate nanoparticles of 20-50 nm diameters as observed by transmission electron microscopy (TEM, FIG. 1(a)). The as-prepared ATCP exhibited a specific surface area of 78 (±3%) m$^2$ g$^{-1}$ resulting in a calculated primary particle diameter ($d_{BET}$) of 25 nm. X-ray disk centrifugation revealed an unimodal size distribution with a mean particle diameter ($d_{XDC}$) of 40 nm as shown in FIG. 1(b). The average number of primary particles per aggregate ($n_p$) was therefore calculated to 2.4. X-ray powder diffraction (XRD) showed no distinct pattern for the as-prepared powder indicating the presence of an amorphous structure. The broad unspecific peaks in the FTIR spectrum corroborated the amorphous state of the material. After sintering (900° C., 30 min) distinct absorption bands characteristic for β-TCP [15] were observed in agreement with earlier studies [3]. FTIR absorption around 1400-1500 cm$^{-1}$ indicate the presence of minute amounts of carbonate in the as-prepared material. Since the absorption peaks at 1215 cm$^{-1}$ to 1140 cm$^{-1}$, at 727 and 496 cm$^{-1}$ are absent, the presence of calcium pyrophosphate, a major impurity in commercial TCP, is excluded.

Figure 2:
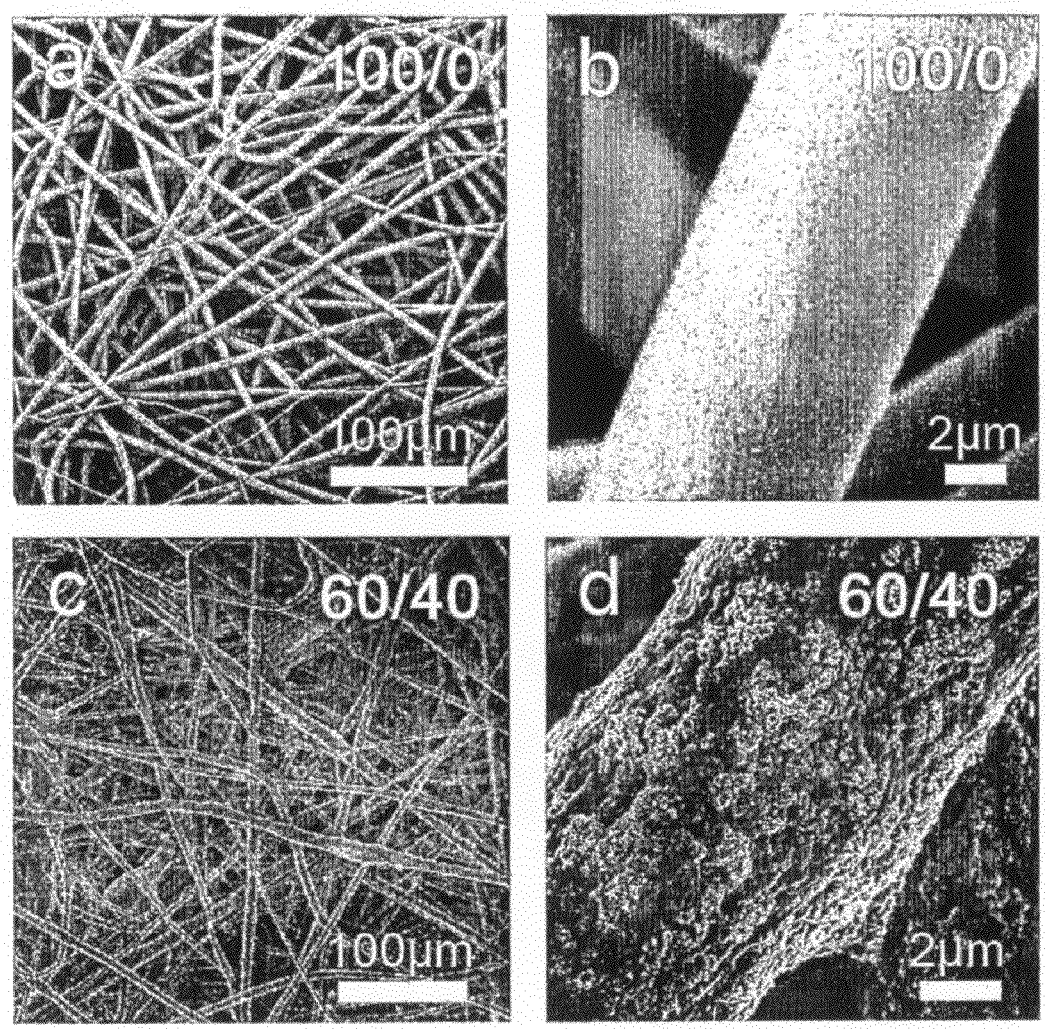
FIG. 2 shows scanning electron microscopy images of as-electrospun scaffolds: PLGA/ATCP 100:0 overview (a) and close-up (b), PLGA/ATCP 60:40 overview (c) and close-up (d).

7. Characterization of the PLGA/TCP Scaffolds: The as-electrospun scaffold can be manually uncompressed into a cotton-like biomaterial (FIG. 1(c)). Test of the post-treated scaffold to fill sockets or defects with hindered accessibility will be discussed at a later stage of this work. SEM micrographs (FIGS. 2(a), (c)) of the as-spun materials show homogenous three-dimensional fibrous meshes for both pure PLGA and PLGA/ATCP scaffolds with a thickness of about 250 μm. The scaffold predominately consists of fibers within a diameter range of 5-10 μm and porosities of 90±3%. The surface of the pure, non-degraded polymer fibers is smooth (FIG. 2(b)) but gets rough by increasing the amount of ATCP nanoparticles (FIG. 2(d)). These small features in the submicron range arise from incorporated agglomerates of nanoparticles exposed to the surface resulting in a strongly increased exchange surface. Incorporation of particles already had major influence on the scaffold precursor and therefore the synthesis parameters. The viscosity of the PLGA/ATCP 60:40 electrospinning solution measured at shear rates between $10\ s^{-1}$ and $100\ s^{-1}$ was 2-3 times higher compared to the other electrospinning solutions (FIG. 7a). To avoid drop formation at the capillary tip the feeding rate for PLGA/ATCP 60:40 was adjusted to lower values (2 ml/h instead of 4 ml/h for all other samples) which would theoretically result in thinner fibers. The lower feed rate was compensated by decreasing the distance between the needle and the collection tube (from 20 cm to 10 cm) in order to obtain consistent scaffold properties without undesired morphology changes [4]. Contact angle measurements on the films prepared from the electrospinning solutions showed that the hydrophilicity of the pure PLGA)(76±1°) is significantly higher compared to the PLGA/ATCP 60:40 nanocomposite)(52±7°). This fact was reflected by the facilitated soaking of the particle-containing scaffolds in SBF if compared to the reference (PLGA/ATCP 100:0). Gel permeation chromatography demonstrated that during the 2 hours UV-sterilization of the scaffolds the peak molar mass ($M_p$) and weight average ($M_w$) values decreased significantly and stayed within the error of measurement during degradation for up to 360 h (table 1). However for the present study the decreased molar mass which mainly affected the mechanical properties is of minor importance since the material is not designated for the application in load bearing bone sites. Although the results observed in tensile test might be helpful to elucidate the later findings during degradation of the scaffolds. Generally, the Young's modulus of the as-electrospun, non-sterilized PLGA/ATCP nanocomposites is steadily decreasing with the incorporation of tricalcium phosphate nanoparticles (FIG. 7b). This could be attributed to the insufficient bonding of PLGA to the ATCP surface creating small fractures although a surfactant (Tween20) is used but is not covalent-bonded to the ATCP surface. UV-sterilization followed by degradation for 15 h has a negative effect on mechanical properties for pure PLGA demonstrated by a 50% decrease of elastic modulus. On the contrary the Young's modulus for sample PLGA/ATCP 60:40 increased during this time by 70%.

TABLE 1

Gel permeation chromatography shows the effect of UV sterilization and degradation on the peak ($M_p$) and weight average ($M_w$) molar mass of pure PLGA and PLGA/ATCP 60:40 scaffolds.

| Sample | $M_p$ (g/mol)$^a$ | $M_w$ (g/mol)$^a$ |
|---|---|---|
| PLGA | 314'000 | 254'000 |
| PLGA, 2 h UV | 72'000 | 57'000 |
| PLGA, 2 h UV, 360 h deg | 73'000 | 59'000 |
| 60/40 | 287'000 | 171'000 |
| 60/40, 2 h UV | 74'000 | 61'000 |
| 60/40, 2 h UV, 360 h deg | 112'000 | 81'000 |

$^a$error ± 10%

8. In vitro degradation experiments: During the immersion in simulated body fluid, two processes occur simultaneously changing the structure as well as the composition of the polymer composite. Polymer degradation removes PLGA mass while the deposition of hydroxyapatite on the surface of the fibers increases the sample mass. Sterile conditions ensured that no bacterial or fungal degradation contributed to polymer dissolution. The change in surface topography was investigated using scanning electron microscopy (SEM). After 45 h degradation, small holes were observed on the surface of the pure polymer fibers (FIG. 3(a)), which might result from the release of water soluble Tween20: In contrast, the scaffold with 40 wt % ATCP showed the formation of a continuous, nano-featured hydroxyapatite layer with a thickness of about 1 μm as shown in a cross section of a fiber (FIG. 3(b)). The inner part of the degraded fiber still seems to contain ATCP particles incorporated in PLGA (FIG. 3(b) inset). Disk-like hydroxyapatite nanocrystals cover the surface and form a cauliflower structure which indicates the steadily deposition of the material starting from a single crystallization site (FIG. 3(c)). After 360 h of degradation the thickness of the hydroxyapatite layer grew up to 2 μm for PLGA/ATCP 60:40. The fact that the deposition of hydroxyapatite occurs only on ATCP doped polymer indicates the important role of ATCP as a precursor of hydroxyapatite formation. In earlier studies [7, 8, 16] on the formation of hydroxyapatite in buffered solutions a solution-mediated, autocatalytic mechanism was proposed and a thermodynamic analysis for equilibriums was accomplished. Initially, amorphous calcium phosphate has to precipitate which subsequently transforms to crystalline apatite. More specific investigation was done on the degraded PLGA/ATCP scaffold by extracting the polymer with chloroform and conducting scanning electron microscopy with the centrifuged, dried residual. Intact hydroxyapatite tubes (FIG. 4) were observed corroborating the dense stable HAp layer formation (FIG. 4(a)). The diameter of the tubes (~5 μm) stays in line with the covered fibers observed directly after degradation (FIG. 4(b)). In order to further investigate the inorganic deposits, the composition of the samples before and after degradation was examined using X-ray powder diffraction (XRD) (FIG. 5(a)). ATCP doped samples showed a broad diffraction peak at a 2θ value of 31.8° which is characteristic for hydroxyapatite. This peak continuously grew with degradation time, while for pure PLGA no diffraction pattern was observed over the investigated period of time. Compared to the crystalline reference pattern showing distinct peaks the deposited HAp exhibits low crystallinity. The unresolved, broad diffraction signals resemble the patterns of poorly crystalline, nano-sized apatite present in bone mineral.

The change in mass of the different scaffolds was followed during degradation. In a typical experiment (SBF changed after 160 h) the mass of pure PLGA is slightly decreasing (−4 wt % after 360 h) possibly because of polymer degradation (FIG. 5(b)). For the fibers according to the invention, the mass increased with both degradation time and amount of incorporated ATCP nanoparticles. This change in mass was mainly attributed to the formation of hydroxyapatite. The sample PLGA/ATCP 90:10 illustrates the two competing processes of polymer degradation for the first two collection intervals and hydroxyapatite deposition. The latter prevails (44 wt % gain after 15 days) most likely after the initially PLGA-covered ATCP particles become more accessible by polymer degradation and now being able to trigger HAp formation. For both high loaded scaffolds the mass increased already after 15 h owing to the facilitated accessibility of ATCP. A final mass gain of 51% and 65% was measured for samples PLGA/ATCP 80:20 and 60:40, respectively.

It is noticeable that the rate of mass gain for samples 80:20 and 60:40 clearly slowed down after 45 h but again increased after the SBF was changed at 160 h. Hence it was assumed that equilibrium conditions for calcium and phosphate ions were reached, below which amorphous calcium phosphate can not precipitate anymore or at a highly decreased rate and as a result subsequent transformation to hydroxyapatite does not take place. In order to have a constant liquid composition, the SBF was changed every 45 h as this seemed reasonable from the other experiments. Indeed, the mass gain for sample PLGA/ATCP 60:40 did not level but increased linearly over time resulting in a 175% mass increase after 15 days (FIG. 7c). Under the assumption of sole HAp formation by ATCP an increasing mass of no more than 90% could be obtained. The observed mass gain strongly indicates that the incorporated ATCP plays the role of an inducer for the precipitation of amorphous calcium phosphate. On one hand the nano-featured surface of ATCP doped scaffolds (FIG. 2(d)) might favor precipitation of hydroxyapatite precursors from solution. On the other hand it is assumed that the highly active ATCP dissolved enhancing the calcium and phosphate concentration near the surface of the fibers and hence triggering the formation of hydroxyapatite. Once the nano-featured hydroxyapatite is built up (after about 45 h), the precipitation proceeds favored by the extremely high surface area (FIGS. 3(c) and 4(a)).

A more detailed picture of the remaining inorganic content could be obtained by sintering degraded PLGA/ATCP 60:40 samples (SBF changed every 45 h) at 1000° C. following examination by X-ray powder diffraction (FIG. 5(c)). The increasing ratio between distinct patterns characteristic for hydroxyapatite and remaining TCP present in the β-phase is in agreement with the observed mass gain. Distinct peaks for β-TCP barely lose intensity over degradation time corroborating the formed core-shell structured fibers which still contain ATCP in the inner part. In addition, this result confirms the importance of ATCP particles predominately at an initial stage of immersion as long as the surface accessibility is not hindered by the newly formed bone-like material.

Thermo-gravimetric analysis coupled with mass spectroscopy further allowed the determination of inorganic content after degradation for 15 days as well as the detection of volatile products formed by heating up the sample to 700° C. (FIG. 7d). A mass loss of 5 wt % for sample 60:40 and of 2 wt % for pure PLGA up to 150° C. was attributed to physisorbed water. At around 300° C. the organic polymer burned off releasing carbon dioxide and water. The inorganic contents in percent (related to the total weight before degradation) after degradation including the remaining ATCP and the deposited hydroxyapatite are shown in FIG. 5(d). An increase of the inorganic content was attributed to the deposition of hydroxyapatite. Starting from 35 wt % inorganics for sample PLGA/ATCP 60:40 before degradation, the value increased linearly to 193 wt % within 15 days (SBF changed every 45 h). In contrast, the inorganic content in pure polymer scaffold was less than 0.5 wt % before and after degradation lying within the error of measurement. The clear deviation from linearity of the inorganic content after 45 h further confirmed the slow down of hydroxyapatite deposition for a delayed SBF change (160 h).

9. Flexibility and compressibility: Simulation of bone defect repair. An advantage of the present electrospun nanocomposite to existing bone graft substitutes is its facile, manual processing into a compressible, easy to apply bone cotton material (FIG. 1(c)). The evaluation of its application was done using simulated bone defect sites with hindered accessibility as it might exist in practical surgical situations (FIG. 6). Defects with different opening diameters $ø_B$ (3-8 mm) and depths $l_B$ (5-40 mm) can be completely filled with the prepared bone cotton within minutes. No preform of the defect has to be made which prolongs surgery and in case of misplacement the bone cotton can be removed entirely in one piece. The packing density can be determined in advance by the weight of the applied bone cotton and the void volume to fill.

The following references provide additional information and are incorporated by reference to the present invention:

[1] Ambrosio A M A, Sahota J S, Khan Y and Laurencin C T 2001 A novel amorphous calcium phosphate polymer ceramic for bone repair: 1. Synthesis and characterization *J. Biomed. Mater. Res.* 58 295-301
[2] Khan Y M, Katti D S and Laurencin C T 2004 Novel polymer-synthesized ceramic composite-based system for bone repair: An in vitro evaluation *J. Biomed. Mater. Res. Part A* 69A 728-37
[3] Loher S, Reboul V, Brunner T J, Simonet M, Dora C, Neuenschwander P and Stark W J 2006 Improved degradation and bioactivity of amorphous aerosol derived tricalcium phosphate nanoparticles in poly(lactide-co-glycolide) *Nanotechnology* 17 2054-61
[4] Zuo W W, Zhu M F, Yang W, Yu H, Chen Y M and Zhang Y 2005 Experimental study on relationship between jet instability and formation of beaded fibers during electrospinning *Polym. Eng. Sci.* 45 704-09
[5] Teo W E and Ramakrishna S 2006 A review on electrospinning design and nanofibre assemblies *Nanotechnology* 17
[6] Stark W J, Pratsinis S E, Maciejewski M, Loher S and Baiker A 2005 Falme synthesis of metal salt nanoparticles, in particular calcium and phosphate comprising nanoparticles patent WO2005/087660 A1
[7] Meyer J L and Eanes E D 1978 Thermodynamic Analysis of Secondary Transition in Spontaneous Precipitation of Calcium-Phosphate *Calcified Tissue Research* 25 209-16
[8] Meyer J L and Eanes E D 1978 Thermodynamic Analysis of Amorphous to Crystalline Calcium-Phosphate Transformation *Calcified Tissue Research* 25 59-68
[9] Pratsinis S E 1998 Flame aerosol synthesis of ceramic powders *Prog. Energy Combust. Sci.* 24 197-219
[10] Limbach L K, Li Y C, Grass R N, Brunner T J, Hintermann M A, Muller M, Gunther D and Stark W J 2005 Oxide nanoparticle uptake in human lung fibroblasts: Effects of particle size, agglomeration, and diffusion at low concentrations *Environmental Science & Technology* 39 9370-76
[11] Kruis F E, Kusters K. A, Pratsinis S E and Scarlett B 1993 A Simple-Model for the Evolution of the Characteristics of Aggregate Particles Undergoing Coagulation and Sintering *Aerosol Sci. Technol.* 19 514-26

[12] Larsen G, Spretz R and Velarde-Ortiz R 2004 Use of coaxial gas jackets to stabilize Taylor cones of volatile solutions and to induce particle-to-fiber transitions *Adv. Mater.* 16 166

[13] Fischbach C, Tessmar J, Lucke A, Schnell E, Schmeer G, Blunk T and Gopferich A 2001 Does UV irradiation affect polymer properties relevant to tissue engineering? *Surf. Sci.* 491 333-45

[14] Oyane A, Kim H M, Furuya T, Kokubo T, Miyazaki T and Nakamura T 2003 Preparation and assessment of revised simulated body fluids *J. Biomed. Mater. Res. Part A* 65A 188-95

[15] Jillavenkatesa A and Condrate R A 1998 The infrared and Raman spectra of beta- and alpha-tricalcium phosphate (Ca-3(PO4)(2)) *Spectr. Lett.* 31 1619-34

[16] Boskey A L and Posner A S 1973 Conversion of Amorphous Calcium Phosphate to Microcrystalline Hydroxyapatite—Ph-Dependent, Solution-Mediated, Solid-Solid Conversion *J. Phys. Chem.* 77 2313-17

Emmerich D, Att W, Stappert C, Sinus floor elevation using osteotomes: a systematic review and meta-analysis, J Periodontol. 2005 August; 76 (8):1237-51

Garg A K., Augmentation grafting of the maxillary sinus for placement of dental implants: anatomy, physiology, and procedures, Implant Dent. 1999; 8 (1):36-46

Lazzara R J., The sinus elevation procedure in endosseous implant therapy. Curr Opin Periodontol. 1996; 3:178-83

Esposito M, Grusovin M G, Worthington H V, Coulthard P., Interventions for replacing missing teeth: bone augmentation techniques for dental implant treatment. Cochrane Database Syst Rev. 2006 Jan. 25; (1):CD003607

Hammerle C H, Jung R E, Feloutzis A., A systematic review of the survival of implants in bone sites augmented with barrier membranes (guided bone regeneration) in partially edentulous patients, J Clin Periodontol. 2002; 29 Suppl 3:226-31

Fiorellini J P, Nevins M L., Localized ridge augmentation/preservation. A systematic review, Ann Periodontol. 2003 December; 8 (1):321-7

Schmidlin P R, Jung R E, Schug J., Prevention of alveolar ridge resorption after tooth extraction—a review, Schweiz Monatsschr Zahnmed. 2004; 114 (4):328-36.

Needleman I G, Worthington H V, Giedrys-Leeper E, Tucker R J., Guided tissue regeneration for periodontal infra-bony defects, Cochrane Database Syst Rev. 2006 Apr. 19; (2): CD001724

Novaes A B Jr, Palioto D B, de Andrade P F, Marchesan J T., Regeneration of class II furcation defects: determinants of increased success, Braz Dent J. 2005; 16 (2):87-97

Murphy K G, Gunsolley J C., Guided tissue regeneration for the treatment of periodontal intrabony and furcation defects. A systematic, review, Ann Periodontol. 2003 December; 8 (1):266-302

Mehra P, Murad H., Maxillary sinus disease of odontogenic origin, Otolaryngol Clin North Am. 2004 April; 37 (2): 347-64

Thoma K, Pajarola G F, Gratz K W, Schmidlin P R., Bioabsorbable root analogue for closure of oroantral communications after tooth extraction: a prospective case-cohort study, Oral Surg Oral Med Oral Pathol Oral Radiol Endod. 2006 May; 101 (5):558-64

Goldberg M, Lacerda-Pinheiro S, Jegat N, Six N, Septier D, Priam F, Bonnefoix M, Tompkins K, Chardin H, Denbesten P, Veis A, Poliard A., The impact of bioactive molecules to stimulate tooth repair and regeneration as part of restorative dentistry. Dent Clin North Am. 2006 April; 50 (2):277-98

He J., Recent advances and future directives in pulp biology, Pract Proced Aesthet Dent. 2006 January-February; 18 (1):49-50, 52

Nakashima M, Akamine A., The application of tissue engineering to regeneration of pulp and dentin in endodontics, J Endod. 2005 October; 31 (10):711-8

The invention claimed is:

1. A method of treatment of bone defects in dental related applications comprising the step of applying a composition in the form of fibers said composition comprising:
   i) one or more biodegradable polymers selected from the group consisting of polymers or copolymers of glycolic acid and/or lactic acid; and
   ii) biodegradable inorganic nanoparticles consisting of XRD amorphous tricalcium phosphate (TCP) having a mean primary particle size below 500 nm; and
   iii) optionally one or more pharmaceutically active ingredients and/or proteins
   to a subject in need of such treatment.

2. A method for the treatment of bone defects in dental related applications comprising the step of applying a yarn said yarn consisting essentially of one or more fibers comprising:
   i) one or more biodegradable polymers selected from the group consisting of polymers or copolymers of glycolic acid and/or lactic acid; and
   ii) biodegradable inorganic nanoparticles consisting of XRD amorphous tricalcium phosphate (TCP) having a mean primary particle size below 500 nm; and
   iii) optionally one or more pharmaceutically active ingredients and/or proteins
   to a subject in need of such treatment.

3. A method for the treatment of bone defects in dental related applications comprising the step of applying a woven fabric said fabric
   consisting essentially of fibers comprising i) one or more biodegradable polymers selected from the group consisting of polymers or copolymers of glycolic acid and/or lactic acid; and
   ii) biodegradable inorganic nanoparticles consisting of XRD amorphous tricalcium phosphate (TCP) having a mean primary particle size below 500 nm; and
   iii) optionally one or more pharmaceutically active ingredients and/or proteins
   to a subject in need of such treatment.

4. A method for the treatment of bone defects in dental related applications comprising the step of applying a fibrous web, said web consisting essentially of fibers comprising i) one or more biodegradable polymers selected from the group consisting of polymers or copolymers of glycolic acid and/or lactic acid; and
   ii) biodegradable inorganic nanoparticles consisting of XRD amorphous tricalcium phosphate (TCP) having a mean primary particle size below 500 nm; and
   iii) optionally one or more pharmaceutically active ingredients and/or proteins
   said web having a bulk density between 0.001-1.7 mg/cm$^3$
   to a subject in need of such treatment.

5. The method according to claim 1 wherein said biodegradable inorganic nanoparticles consisting of XRD-amorphous TCP has some or all of the Ca-ions stoichiometrically replaced by one or more elements selected from the group comprising strontium, magnesium, sodium, potassium, bismuth, barium, gadolinium, europium, holmium, neodymium or praseodymium.

6. The method according to claim 1 wherein said biodegradable inorganic nanoparticles consisting of XRD-amorphous TCP has up to 0.5 mass-% of the Ca-ions replaced by Ag-ions.

7. The method according to claim 1 wherein said pharmaceutically active ingredients are selected from the group consisting of anti-microbiotic, anti-fungal, anti-inflammatory and immunosuppressive active ingredients.

8. The method according to claim 1 wherein said proteins are selected from the group of proteins that support bone healing and/or proteins that influence the differentiation of bone marrow stem cells to osteoclasts/osteoblasts.

9. The method according to claim 1 wherein at least 90 mass-% of said fibers have a diameter of 1-50 um.

10. The method according to claim 1 wherein said inorganic nanoparticles are homogeneously distributed within said biodegradable polymer.

* * * * *

UNITED STATES PATENT AND TRADEMARK OFFICE
CERTIFICATE OF CORRECTION

PATENT NO. : 8,282,911 B2  
APPLICATION NO. : 12/446558  
DATED : October 9, 2012  
INVENTOR(S) : Stark et al.

Page 1 of 1

It is certified that error appears in the above-identified patent and that said Letters Patent is hereby corrected as shown below:

In the Claims

In Column 20, Line 9, in Claim 1, delete "method of" and insert -- method for the --, therefor.

Signed and Sealed this
Twenty-first Day of October, 2014

Michelle K. Lee
*Deputy Director of the United States Patent and Trademark Office*